(12) United States Patent
Burgass et al.

(10) Patent No.: US 6,298,724 B1
(45) Date of Patent: Oct. 9, 2001

(54) CLATHRATE HYDRATE DISSOCIATION POINT DETECTION AND MEASUREMENT

(75) Inventors: Rhoderick William Burgass; Adrian Christopher Todd; Sayed Ali Danesh; Bahman Tohidi Kalorazi, all of Edinburgh (GB)

(73) Assignee: Heriot-Watt University (GB)

( * ) Notice: Subject to any disclaimer, the term of this patent is extended or adjusted under 35 U.S.C. 154(b) by 0 days.

(21) Appl. No.: 09/402,389

(22) PCT Filed: Apr. 6, 1998

(86) PCT No.: PCT/GB98/01005

§ 371 Date: Dec. 27, 1999

§ 102(e) Date: Dec. 27, 1999

(87) PCT Pub. No.: WO98/45692

PCT Pub. Date: Oct. 15, 1998

(30) Foreign Application Priority Data

Apr. 5, 1997 (GB) .................................................. 9706991

(51) Int. Cl.[7] .............................. G01H 9/00; G01N 13/04
(52) U.S. Cl. ......................... 73/579; 73/61.45; 73/61.47; 73/53.01
(58) Field of Search .................................. 73/570, 24.01, 73/53.01, 19.01, 61.45, 599, 597; 422/68.1, 69

(56) References Cited

U.S. PATENT DOCUMENTS

| | | | |
|---|---|---|---|
| 4,461,178 | 7/1984 | Chamuel | 73/599 |
| 5,151,110 | 9/1992 | Bein et al. | 95/140 |
| 5,187,980 | 2/1993 | Blair et al. | 73/599 |
| 5,635,631 | 6/1997 | Yesudas et al. | 73/61.46 |
| 5,659,129 | 8/1997 | Asoyan et al. | 73/54.25 |
| 6,180,843 | 1/2001 | Heinemann et al. | 585/15 |
| 6,223,588 | 5/2001 | Burgass et al. | 73/53.01 |

FOREIGN PATENT DOCUMENTS 61023955A 1/1986 (JP) .

OTHER PUBLICATIONS

G.D. Holder et al., "Hydrate dissociation pressures of (methane +ethane +water) existence of a locus of Minimum pressures" *J. Chem. Thermodynamics*, vol. 12, No. 7, 1980, London, GB, pp. 1093–1104.

A. Danesh et al., "Hydrate Equilibrium Data of Methyl Cyclopentane With Methane or Nitrogen", *Trans . . . IchemE.*, vol. 72, No. a, 1994, pp. 197–200.

L. Alfonso et al., "A quartz crystal microbalance to determine enthalpies of sublimation at intermediate Temperatures by the Knudsen effusion method", *Measurement Science and Technology*, vol. 5, No. 1, Jan. 1, 1994, pp. 51–54.

International Search Report, PCT/GB98/01005, dated Aug. 14, 1998.

*Primary Examiner*—Hezron Williams
*Assistant Examiner*—Jacques Saint-Surin
(74) *Attorney, Agent, or Firm*—Wolf, Greenfield & Sacks, P.C.

(57) ABSTRACT

Apparatus and method for detecting the formation and dissociation of gas hydrates in a fluid. The apparatus used comprises a piezoelectric crystal sensor and a signal analyzer. The crystal sensor has a deposition surface in contact with the fluid. Under a range of pressures and or temperatures the resonant frequency or an electrical parameter dependent on the resonant frequency of the piezoelectric sensor is measured. There is a step change in the resonant frequency which occurs upon the formation or dissociation of a clathrate hydrate on the deposition surface, so that the formation or dissociation of said clathrate hydrate may be detected.

34 Claims, 3 Drawing Sheets

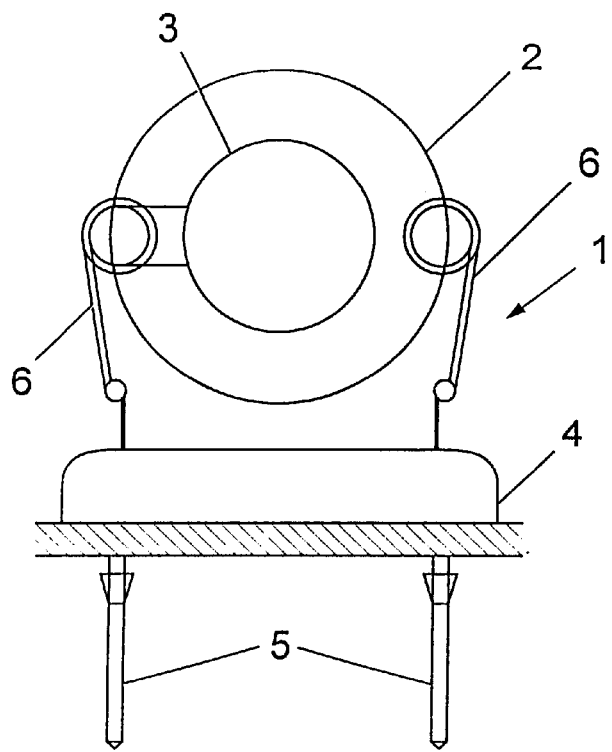
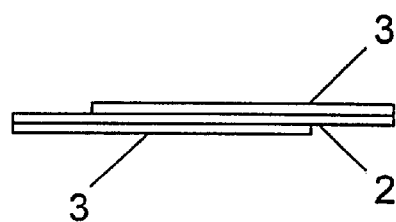
Fig. 1b
Fig. 1a
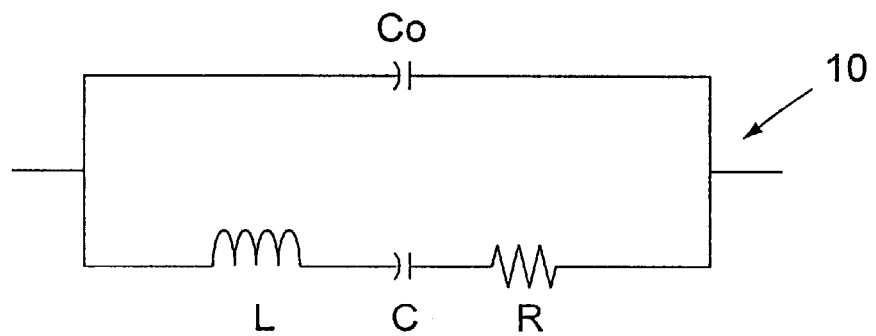
Fig. 2

CLATHRATE HYDRATE DISSOCIATION POINT DETECTION AND MEASUREMENT

The present invention relates to the detection of the dissociation of clathrate hydrates and in particular, but not exclusively, to the measurement of pressures and corresponding temperatures at which clathrate hydrates are found to dissociate.

Clathrate hydrates of gases are formed when, under favourable temperature and pressure conditions, gas molecules become encapsulated in crystalline structures of water. The water forms a cage-like structure around guest molecules. Chlorine hydrates were first discovered in 1810 and following this many compounds which form clathrate hydrates have been identified. In 1934 it was discovered that gas clathrate hydrates were causing blocking of natural gas transmission lines and for this reason research aimed at understanding and resolving this problem was initiated and continues today. Apart from being considered as a problem in the oil industry, clathrate hydrates are considered important for a number of reasons such as a potential source of energy, and for use in processes such as desalination and gas transportation.

Clathrate hydrates, especially in the oil industry, are often referred to as gas hydrates, or simply as hydrates. Gas hydrates of interest, particularly with respect to producing, transporting and processing of natural gas and petroleum fluids, are composed of water and the following eight guest molecules: methane, ethane, propane, isobutane, normal butane, nitrogen, carbon dioxide and hydrogen sulphide. Other guest molecules capable of forming clathrate hydrates include ethane, nitrous oxide, acetylene, vinyl chloride, methyl bromide, ethyl bromide, cyclopropane, methyl mercaptan, sulphur dioxide, argon, krypton, oxygen, xenon, trimethylene oxides and others. Clathrate hydrate formation is a possibility wherever water exists in the presence of such molecules, both naturally and artificially, at temperatures above 0° C. and below 0° C., when pressure is elevated.

It is primarily due to their crystalline, insoluble, non-flowing nature that hydrates have been of interest to industry. They are a source of problems, because they block transmission lines, plug Blow Out Preventers, jeopardize the foundations of deepwater platforms and pipelines, collapse tubing and casing, and foul process heat exchangers and expanders. Common methods of preventing hydrate formation are the regulation of pipeline water content, the use of special drilling mud compositions and the injection of Large quantities of methanol into pipelines. All these methods are costly and complex, so there is a need to know more about the likelihood of clathrate formation in a particular sample.

The point (in terms of pressure and temperature) at which, in a system containing a clathrate hydrate, the hydrate dissociates is known as the dissociation point.

The pressure at which a clathrate hydrate dissociates at a given temperature is referred to as the dissociation pressure (DP) for that temperature, while the temperature at which the hydrate dissociates for a given pressure is referred to as the dissociation temperature (DT) for that pressure. The DP and DT are important factors to be determined in order to identify and characterise the nature and properties of any clathrate hydrate.

Previously, the DP or DT of a given hydrate has been determined using methods dependent on visual identification of clathrate formation/dissociation, which are prone to human error and are inherently inaccurate. Measurements of the DT have also been made by mixing a test fluid with water, supercooling the mixture till the clathrate is formed, and then slowly warming the clathrate and detecting and/or measuring the increase in pressure which results from gas molecules escaping from inside the clathrate upon its dissociation. The latter method suffers from the problem of being extremely time consuming since the time taken for a system containing a sufficiently large sample of the (solid phase) clathrate to reach equilibrium at each desired temperature measurement is significant, in some cases a number of weeks.

It is an aim of the present invention substantially to avoid or minimise one or more of the foregoing disadvantages.

According to a first aspect of the present invention we provide an apparatus suitable for use in detecting the formation of, and/or the onset of dissociation of, clathrate hydrates, the apparatus comprising: a piezoelectric crystal sensor which is formed and arranged to resonate at a variable frequency which is dependent upon a mass loading on a deposition surface thereof; and signal analyser means formed and arranged for monitoring, in use of the apparatus, directly or indirectly, change in the resonant frequency of the piezoelectric crystal sensor while one of the temperature and pressure of a test sample in contact with the deposition surface of the sensor is varied, so as to detect a substantial change in said resonant frequency occurring upon the formation or dissociation of a clathrate hydrate on the deposition surface, whereby the formation or dissociation of said clathrate hydrate may be detected.

One advantage of the apparatus of the invention is that it enables the dissociation (or the formation) of clathrate hydrates to be detected very accurately. Unlike the aforementioned prior art, the invention does not rely on visual identification methods, or the detection of small pressure increases.

According to a second aspect of the invention we provide an apparatus for measuring dissociation point temperatures and pressures of clathrate hydrates, the apparatus comprising: a piezoelectric crystal sensor which is formed and arranged to resonate at a variable frequency which is dependent upon a mass loading on a deposition surface thereof; a pressure vessel having a pressure chamber defined therein, said piezoelectric crystal sensor being mounted in the pressure chamber, and the pressure vessel having inlet means via which a test fluid may be introduced into the pressure chamber of the vessel; temperature control means for controlling the temperature in the pressure chamber; pressure control means for controlling the pressure in the chamber; signal analyser means formed and arranged for monitoring, in use of the apparatus, directly or indirectly, change in the resonant frequency of the piezoelectric crystal while one of the temperature and pressure of test fluid in contact with the deposition surface of the sensor is varied, so as to detect a substantial change in said resonant frequency occurring upon the formation or dissociation of a clathrate hydrate on the deposition surface, whereby the formation or dissociation of said clathrate hydrate may be detected; and temperature measuring means and pressure measuring means for measuring the temperature and pressure in the chamber at least when the dissociation of said clathrate hydrate is detected.

An advantage of the apparatus of present invention is that only a relatively small amount of the test fluid is required since only a small amount of clathrate hydrate need be formed in the apparatus of the invention in comparison with the prior art techniques which rely on visual identification of clathrate formation and dissociation, or detection of pressure changes due to clathrate hydrate formation/dissociation, and thus require much larger amounts of clathrate hydrates to be present. In consequence, another advantage of the apparatus is that it enables the DT or DP to be measured relatively quickly in comparison with the afore-mentioned prior art methods which required relatively large samples of clathrate hydrate (in which equilibrium conditions for a given temperature and pressure can take a very long time to reach) in order for effects occurring at the dissociation point to be detected.

Said substantial change in the resonant frequency occurring in the resonant frequency may be of the order of a few hundred to a few thousand Hertz. The magnitude of the change may be greater or smaller than this, though, depending on the amount of hydrate formed on the crystal and/or where on the crystal surface the hydrate is situated.

Advantageously, the temperature and pressure measuring means are formed and arranged for continuously measuring temperature and pressure in the pressure chamber, in use of the apparatus.

The piezoelectric crystal sensor preferably comprises a quartz crystal microbalance (QCM). The QCM conveniently comprises an AT-cut quartz crystal sandwiched between excitation electrodes to which a driving signal may be applied to generate a transverse shear wave across the thickness of the crystal. Such a QCM can be made to oscillate even when immersed in fluid (gas or liquid) and will resonate at a frequency which is dependent, among other things, on the mass loading on the crystal. Any change in the mass load on the crystal will change the resonant frequency of the QCM. When a clathrate hydrate forms from a mixture of ice and test fluid on the so-called deposition surface of the crystal, the mass load on the crystal will change significantly and this will, in turn, significantly change the resonant frequency of the QCM. Similarly, a significant change in the resonant frequency will occur when a clathrate hydrate present on the deposition surface of the crystal dissociates.

A further advantage of the present invention is that if, due to a change in the structure of a clathrate hydrate being analysed, a density change in the hydrate occurs, the apparatus according to the invention may be capable of detecting and measuring the point, in terms of pressure and temperature, at which this structural change takes place. Moreover, if more than one clathrate hydrate structures is formed on the deposition surface of the crystal, it may be possible to detect and/or measure the dissociation point temperature/pressure for each such structure.

The signal analyser means is preferably adapted to control the driving signal supplied to the excitation electrodes and may be adapted to, for example, analyse the phase of an electrical impedance or gain of the sensor so as to detect a resonant condition of the sensor (occurring at a resonant frequency of the sensor). Similarly, the resonant condition could be detected by monitoring, for example, current, voltage or electrical conductance of the sensor so as to detect a resonant condition thereof. In use of the apparatus, the signal analyser means is advantageously adapted to produce and detect a resonant condition of the sensor at a predetermined number of different pressures, or temperatures, in the pressure chamber of the pressure vessel.

The analyser means is preferably adapted to measure, and conveniently also to store or record, the value of the (driving) signal frequency, and/or one or more of the sensor current, voltage and conductance, at each detected resonant condition of the sensor. Change in the resonant frequency may thus be monitored directly, or alternatively indirectly by monitoring change in the values of, for example, current, voltage or conductance, at resonant frequency.

Where the piezoelectric crystal sensor comprises a QCM, the quartz crystal incorporated therein is preferably an unpolished quartz crystal. This had the advantage of increasing the likelihood that hydrate(s) which have formed will adhere to the crystal.

In use of the apparatus, test fluid to be analysed is injected or other wise introduced into the pressure chamber so as to surround the piezoelectric crystal sensor. At least a small amount of water is preferably introduced onto said deposition surface of the crystal sensor and frozen prior to introduction of the test fluid to the pressure chamber, in order to allow clathrate hydrates to form. This water may be introduced by, for example, placing one or more drops of water onto the deposition surface of the crystal sensor and lowering the temperature in the pressure chamber so as to freeze the water. The pressure control means may conveniently comprise valve means on the inlet means of the pressure vessel for controlling the injection or release of fluid into or out of the pressure chamber. The pressure vessel may further include outlet means via which fluid contents of the pressure chamber may exit therefrom. Alternatively, or additionally, the pressure control means may comprise pump means for compressing or evacuating fluid in/form the pressure chamber. Pump means may be provided for connection to the outlet means, for evacuating the pressure chamber.

The temperature control means may comprise a water jacket surrounding the pressure vessel. Additionally, or alternatively, the temperature control means may include a heat sink.

The apparatus conveniently includes a pressure vessel mounting means incorporating a pivotal mounting for the pressure vessel, whereby the pressure vessel is pivotally mounted to allow rotation of the vessel, in use of the apparatus, so as to mix the fluid contents of the vessel. Rotating the vessel can reduce the time taken for the contents of the pressure vessel to reach equilibrium.

According to a third aspect of the invention we provide a method of measuring dissociation temperatures and dissociation pressures of a clathrate hydrate, the method comprising the steps of:

a) providing, in a pressure chamber of a pressure vessel, a piezoelectric crystal sensor which is formed and arranged to resonate at a variable frequency which is dependent on a mass loading on a deposition surface thereof;

b) depositing a small amount of water on said sensor deposition surface;

c) lowering the temperature in the pressure chamber below freezing so as to freeze said small amount of water;

d) evacuating the pressure chamber and subsequently introducing therein a test fluid;

e) controlling the temperature and pressure in the pressure chamber so as to achieve clathrate hydrate formation on the deposition surface of the sensor;

f) monitoring, directly or indirectly, change in the resonant frequency of the piezoelectric crystal sensor while said temperature and pressure are controlled, so as to detect a substantial change in said resonant frequency which occurs upon formation of said clathrate hydrate, thereby to deject the formation of said clathrate hydrate;

g) varying one of the temperature and pressure in the pressure chamber, preferably in a step-wise manner, so as to cause dissociation of the clathrate hydrate, while maintaining the other one of the temperature and pressure substantially constant at a predetermined value;

h) monitoring, directly or indirectly, change in the resonant frequency of the piezoelectric crystal sensor while said one of the temperature and pressure is varied, so as to detect a substantial change in said resonant frequency which occurs upon dissociation of the clathrate hydrate, thereby to detect the dissociation of said clathrate hydrate; and j) measuring the magnitude of the varying one of the temperature and pressure when the dissociation of said clathrate hydrate is detected, and the magnitude of the one of the temperature and pressure which is held substantially constant, the measured magnitudes representing one of: the dissociation temperature of said clathrate hydrate at a predetermined pressure, and the dissociation pressure of said clathrate hydrate at a predetermined temperature.

Said small amount of water may be deposited on the sensor deposition surface in a number of possible ways. It is hereby expressly stated that steps (a) and (b) of the above method may be carried out in any order. For example, one or more drops of water may be placed on the deposition surface of the sensor prior to placing the sensor in the pressure chamber of the pressure vessel. Alternatively, water in the form of drops, mist, or liquid could be introduced into the pressure chamber once the sensor has been placed therein, as long as it can be ensured that at least some water will be deposited on the sensor deposition surface. The crystal may additionally be coated with a hygroscopic material for absorbing moisture introduced into the pressure chamber.

Using the above-described method, the dissociation temperature (DT) at a given pressure, or alternatively the dissociation pressure (DP) at a given temperature, may be measured.

Preferably, the temperature and pressure in the pressure chamber are continuously measured, conveniently throughout steps (c) to (j) of the method.

The detection of said substantial change in the resonant frequency may be achieved by recording monitored values of the resonant frequency or, for example, current, voltage or conductance at resonant frequency, and the corresponding varying temperature or pressure values, in graphical form, thereby recording the substantial change in the resonant frequency, or the nominated other electrical property at resonant frequency, occurring at the DT or DP.

The above-described apparatus and method(s) are intended in particular, but exclusively, for laboratory use. e.g. for the determination of dissociation temperatures and pressure of sample clathrate hydrates. It is envisaged that the apparatus could, nevertheless, be used in certain in situ applications, for example in monitoring applications where, for safety reasons or other operating considerations, the detection of the formation of clathrate hydrates is desirable. This could be the detection of the formation of clathrate hydrates in an underground gas pipe, for example, and/or measurement of the dissociation temperature or pressure of clathrate hydrates present in a system in which one of the temperature and pressure is varying while the other one remains substantially constant.

Preferred embodiments of the invention will now be described by way of example only and with reference to the accompanying drawings in which:

FIG. 1(a) is a schematic side view (enlarged) of a quartz crystal microbalance (QCM);

FIG. 1(b) is an end view of the arrangement of the quartz crystal and the electrodes of the QCM of FIG. 1(a);

FIG. 2 is a schematic diagram of the equivalent electrical circuit representing the electrical behaviour of the QCM;

Figure 3:
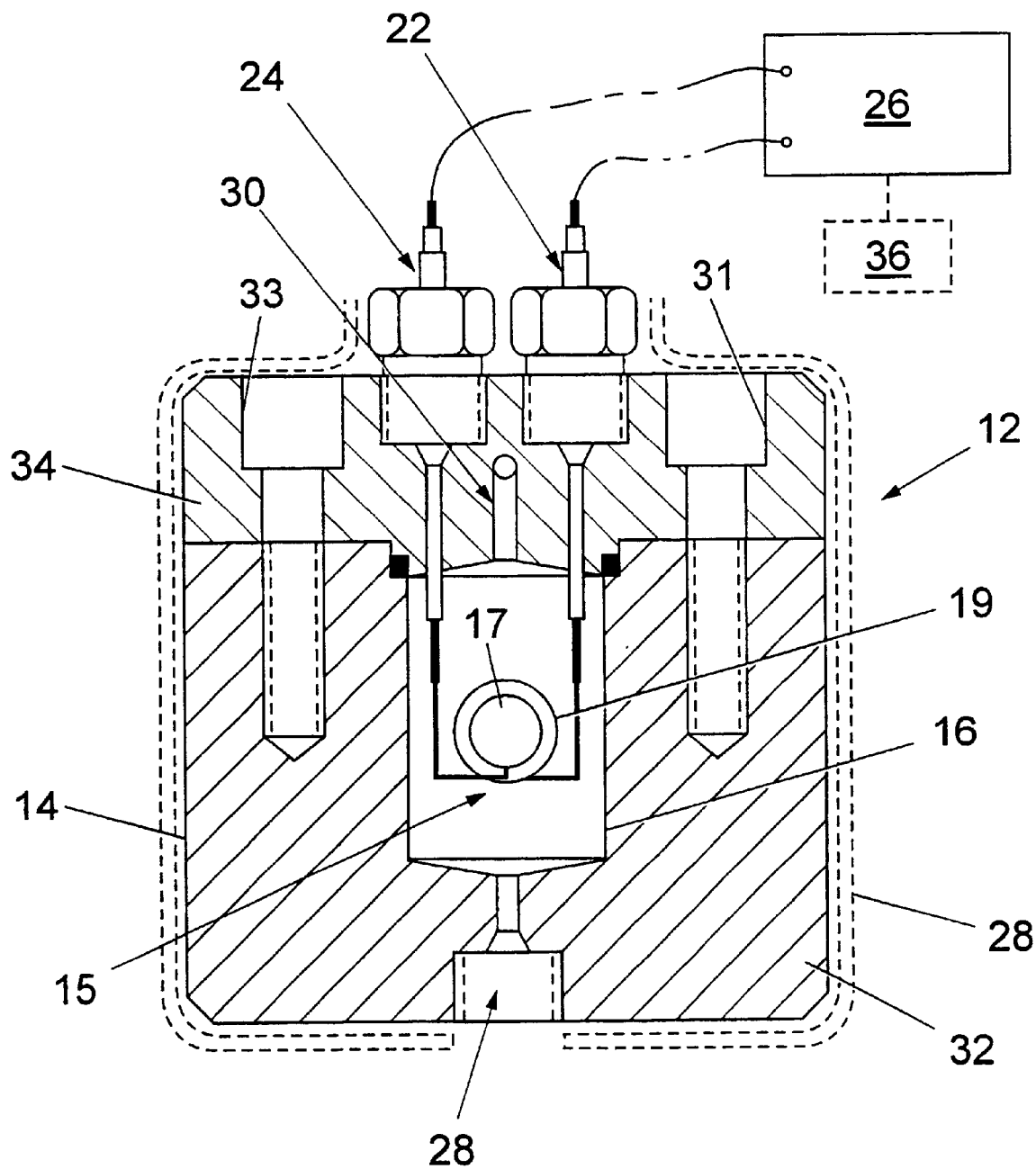
FIG. 3 is a cross-sectional side view through an apparatus 12 according to the invention for detecting and measuring clathrate hydrate dissociation points.
Figure 4:
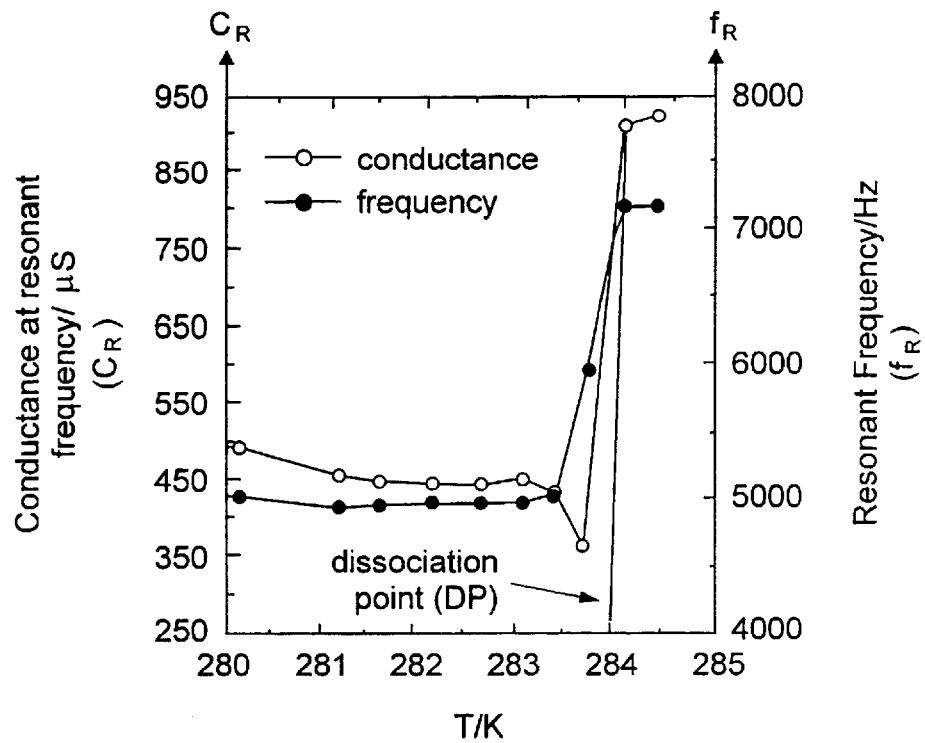
Figure 5:
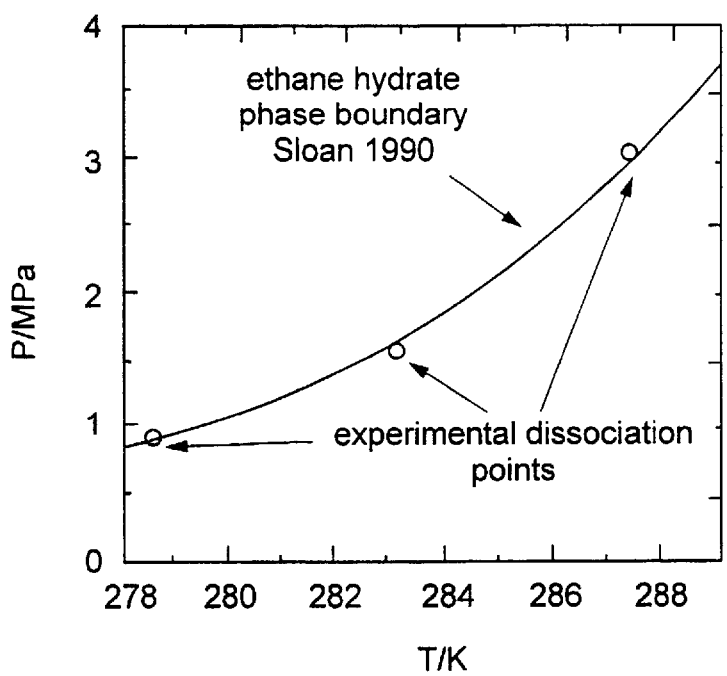

FIG. 4 shows graphs of resonant frequency vs. temperature, and conductance at resonant frequency versus temperature, obtained using the apparatus of FIG. 3, illustrating the dissociation of a clathrate hydrate formed from methane and isopentane, at 8.28 MPascals; and FIG. 5 is a graph of pressure vs. temperature at the hydrate phase boundary for ethane hydrate, comparing theoretical data with experimental data obtained using the apparatus of FIG. 3.

FIG. 1(a) shows schematically a typical Quartz Crystal Microbalance (QCM) 1. The QCM comprises an AT-cut polished quartz crystal 2 sandwiched between two gold excitation electrodes 3 (as shown in detail in FIG. 1(b)) that generate a transverse shear wave across the thickness of the quartz crystal (when a driving electrical signal is applied to the electrodes). The crystal 2 has an inherent resonant frequency at 5 MHz. The crystal 2 is mounted by means of two connecting wires 6 connected to respective ones of the electrodes 3, to a mounting base 4, as shown. Driving signals are applied to the connecting wires 6 via conducting pins 5 which extend through the mounting base 4.

FIG. 2 shoes the elements of an equivalent electrical circuit 10 which the resonant electrical behaviour of the QCM imitates. As shown, the equivalent electrical circuit 10 comprises a resistor R, capacitor C and inductor L, all in series, which are in parallel with an additional capacitance Co which is the static capacitance of the quartz crystal.

FIG. 3 shows a cross-section through an apparatus 12 according to a preferred embodiment of the invention. The apparatus 12 comprises a stainless steel pressure vessel 14 defining an internal pressure chamber 16 of volume 40 cubic centimetres (cc). A QCM 18 is mounted in the pressure chamber 16 The two electrodes 17 (only one shown) of the QCM are gold, are bonded to the surface of the QCM crystal 19, and are connected, via high pressure vessel 14, to an HP 4194A impedance/gain phase analyser 26 (indicated in block form only) located remote from the pressure vessel. The pressure vessel has a sample inlet 28 communicating with the chamber 16 via which inlet test fluid may be introduced to the chamber 16. An outlet 30 is also provided in the pressure vessel via which fluids may exit from the chamber 16. The pressure vessel 14 is mounted on a pivot (not shown) to allow for rotation of the vessel, and thus mixing of the contents of the vessel, so as to help in achieving equilibrium of the contents of the pressure chamber 16. The pressure vessel 14 is also surrounded by a water jacket 28 (indicated in broken lines) for use in controlling the temperature of the contents of the pressure chamber 16. A temperature sensor (not shown) of the platinum resistance probe type is provided in the apparatus, in the water jacket 28, for continuously monitoring the temperature of the water jacket (which is substantially the same, or closely approximates to, the temperature in the pressure chamber). A pressure sensor (not shown) in the form of a strain gauge transducer is located in a branch off the outlet 30 of the pressure vessel and is arranged to continuously monitor the pressure therein.

The pressure vessel 14, as shown in FIG. 3, in fact comprises two separate portions: a main portion 32 having the inlet 28 and largely defining the chamber 16, and a lid portion 34 having the electric feed throughs 22, 24, to which the QCM is attached, and the outlet 30. The lid portion 34 is bolted to the main portion 32, the recessed bolt holes 31, 33 being shown in FIG. 3. In use of the apparatus, a drop of water is placed on one surface of the quartz crystal 19, hereinafter referred to as "the deposition surface", prior to assembling the lid portion 34 to the main portion 32. After bolting the two portions of the pressure vessel together, thereby closing the chamber 16 except to fluids entering or leaving therefrom via the inlet 28 and outlet 30 respectively, the temperature in the chamber 16 is lowered below 0° C., using the water jacket, in order to freeze the drop of water. The chamber 16 is then evacuated using a vacuum pump (not shown) connected to the outlet 30 and a sample of test fluids is then injected or pumped into the chamber 16 via the inlet 28. The chamber pressure P and temperature T are then adjusted using the water jacket and by releasing and/or injecting test fluid into or out of the chamber until conditions favourable for clathrate hydrate formation are achieved. The formation of such hydrates is obvious as it causes significant changes in the resonant frequency, or other electrical properties such as conductance at resonant frequency, which changes can be detected using the phase analyser 26.

Once the formation of clathrate hydrate(s) on the QCM has been detected, dissociation point measurements can then be obtained by, for example, raising the temperature step-wise in the chamber, while keeping the pressure therein substantially constant, and using the phase analyser 26 to monitor the resonant frequency, and/or conductance at resonant frequency, of the QCM at each temperature and to detect any significant changes therein, signalling dissociation of the clathrate hydrate. Alternatively, the temperature may be kept substantially constant while the pressure in the chamber is varied in a step-wise manner and the resonant frequency and/or conductance at resonant frequency is monitored.

FIG. 4 illustrates graphically the detection and measurement of the dissociation temperature, at 8.28 MPascals pressure, for a clathrate hydrate formed from a mixture of methane and isopentane. The temperature in the chamber 16 was varied in a step-wise manner and at each temperature the resonant frequency $f_R$ and the conductance at resonant frequency $c_R$ of the QCM was measured by the phase analyser 26. By plotting a graph of resonant frequency $f_R$ against pressure P, and/or a graph of Conductance $c_R$ at resonant frequency against pressure P, the dissociation of the clathrate hydrate can be seen clearly in the graph as a significant change in the resonant frequency (a change of approx. 2000 Hz), and a significant change in the Conductance at resonant frequency (a change of approx. 550 $\mu S$), occurring substantially at the dissociation temperature (approx. 284 Kelvin). FIG. 5 is a graph of pressure P vs. temperature T plotted using theoretically calculated values for ethane hydrate in the region of the liquid/gas phase boundary. Experimental points obtained from the experimental data collected with the apparatus of the invention are indicated on the graph in FIG. 5 and it can be seen that there is a good agreement between the theoretical and experimental data.

In a further possible embodiment of the invention, the measurements of resonant frequency $f_R$, and Conductance at resonant frequency $c_R$, are recorded by a recording device 36 (e.g. a printer, or a microprocessor with a VDU) connected to the phase analyser 26, as shown in broken lines in FIG. 3.

The invention has other applications, apart from those described above. The method of measuring the hydrate dissociation point of the present invention may be used for the rapid screening of chemicals for both hydrate inhibition and hydrate promotion. Tests were carried out with hydrates formed with methane and cyclopentane, and gave following results. Forming hydrates from water resulted in a drop in conductance of around 90 micro Siemens. Forming hydrates from melting ice and from water with asphaltenes present gave a drop in conductance of around 476 micro Siemens. The drop is related to the conductance measurement when water or water with asphaltene is on the QCM with no hydrate formation. These results show that the formation of hydrates from melting ice or from water with asphaltenes is more efficient. This increase in efficiency is due to the number of nucleation sites in the droplet of water.

The rate of drop in conductance measured in the method of the invention can also be used to show the rate of hydrate formation. The method and apparatus can be used to determine rapidly the efficiency of proposed hydrate inhibitors and/or promoters, using small amounts of sample and with real fluids.

The small volume of sample needed represents a real advantage over prior art methods, which typically would need a sample of 50 cc of fluid. The present invention can be carried out with a small sample, even a drop, on the surface of the crystal. The development of smaller crystal sensors will make the detection of hydrate dissociation points possible with samples whose mass is measured in nanograms.

Further tests with hydrates using the method of the invention have shown that where the cavity occupancy has an influence on the density of the hydrates formed, then this influence can be detected. For example, for hydrates formed from methane and isopentane, below the quintuple point structure H hydrates are formed, composed of water cages with methane and isopentane molecules filling the cavities. Above the quintuple point only structure I hydrates are formed with methane filling the cavities. There is a significant density difference between the two types of hydrates. By shifting the temperature and pressure above and below the quintuple point, the change in structure of the hydrates can be detected, since it results in a significant change in the conductance reading at resonant frequency.

The invention can find an application in the evaluation of surface treatments designed to prevent hydrates sticking.

These and other modifications and improvements can be incorporated without departing from the scope of the invention.

What is claimed is:

1. An apparatus suitable for use in detecting the formation of, and/or the onset of dissociation of, clathrate hydrates, the apparatus comprising:

a pressure vessel defining a chamber for holding a rear sample, a piezoelectric crystal sensor which is formed and arranged to resonate at a variable frequency which is dependent upon a mass loading on a surface of the crystal, the crystal sensor being mounted in the chamber such that a test sample in the chamber may be in direct contact with the surface of the crystal; and signal analyzer means formed and arranged for monitoring, in use of the apparatus, directly or indirectly, change in the resonant frequency of the piezoelectric crystal sensor while one of the temperature and pressure of the test sample in contact with the surface of the crystal is varied, so as to detect a substantial change in said resonant frequency occurring upon the formation or dissociation of a clathrate hydrate in the rest sample in contact with the surface of the crystal, whereby the formation or dissociation of said clathrate hydrate may be detected.

2. Apparatus according to claim 1 wherein the pressure vessel comprises inlet means via which a test fluid may be introduced into the chamber of the vessel.

3. Apparatus according to claim 1 further comprising: temperature control means for controlling the temperature in the chamber.

4. Apparatus according to claim 1 further comprising: pressure control means for controlling the pressure in the chamber.

5. Apparatus according to claim 1 further comprising: at least one of temperature measuring means and pressure measuring means for measuring the temperature and/or pressure in the chamber at least when the dissociation of said clathrate hydrate is detected.

6. Apparatus according to claim 1 wherein the piezoelectric crystal sensor is an acoustic wave sensor selected from the group consisting of thickness-shear-mode (TSM) devices, surface-acoustic-wave (SAW) devices, acoustic-plate-mode (APM) devices and flexural-plate-wave (FPW) devices.

7. Apparatus according to claim 6 wherein the piezoelectric crystal sensor is a quartz crystal microbalance comprising an AT-cut quartz crystal sandwiched between excitation electrodes to which a driving signal may be applied to generate a transverse shear wave across the thickness of the crystal.

8. Apparatus according to claim 7 wherein the signal analyzer means is adapted to control the driving signal supplied to the excitation electrodes.

9. Apparatus according to claim 7 wherein the signal analyzer means is adapted to analyse the phase of an electrical impedance or gain of the sensor so as to detect a resonant condition of the sensor which occurs at a resonant frequency of the sensor.

10. Apparatus according to claim 9 wherein the resonant condition is detected by monitoring current, voltage or electrical conductance of the sensor.

11. Apparatus according to claim 1 wherein the signal analyzer means comprises control means adapted to produce and detect a resonant condition of the sensor at a predetermined number of different pressures, or temperatures, of the fluid in contact with the sensor.

12. Apparatus according to claim 1 wherein the signal analyzer means comprises a driving signal generator and measurement means adapted to measure the frequency of the driving signal and/or one or more of the sensor current, voltage and conductance, at each detected resonant condition of the sensor.

13. Apparatus according to claim 12 wherein the signal analyzer means comprises monitoring means adapted to monitor the change in the resonant frequency.

14. Apparatus according to claim 13 wherein said monitoring means monitors the change in resonant frequency by monitoring the change in the values of current, voltage or conductance, at resonant frequency.

15. Apparatus according to claim 12 wherein the signal analyzer means comprises data storage means for storing and/or recording the value of the driving signal frequency, and/or one or more of the sensor current, voltage and conductance, at each detected resonant condition of the sensor.

16. Apparatus according to claim 1 wherein the signal analyzer means comprises computational means which recognises and calculates the point at which there is a discontinuity in the change of resonant frequency with changing temperature or changing pressure.

17. Apparatus according to claim 16 wherein the discontinuity is a step change in the resonant frequency or a substantial change in the rate of change of resonant frequency with changing temperature or changing pressure.

18. Apparatus according to claim 1 wherein the piezoelectric crystal sensor comprises a quartz crystal having an unpolished quartz crystal surface, to promote the formation of crystals on said surface.

19. Apparatus according to claim 1 further comprising means for introducing a small amount of water onto said deposition surface of the crystal sensor.

20. Apparatus according to claim 1 further comprising valve means for controlling the injection or release of fluid into or out of the chamber.

21. Apparatus according to claim 1 further comprising outlet means via which fluid contents of the chamber may exit therefrom.

22. Apparatus according to claim 1 further comprising pump means for compressing or evacuating fluid in or from the chamber.

23. Apparatus according to claim 1 further comprising a water jacket surrounding the pressure vessel.

24. Apparatus according to claim 1 further comprising a heat sink.

25. Apparatus according to claim 1 wherein the chamber is pivotally mounted to allow rotation of the chamber, in use of the apparatus, so as to mix the fluid contents of the chamber.

26. A method of measuring dissociation temperatures and dissociation pressures of a clathrate hydrate, the method comprising the steps of:

a) providing in a chamber a piezoelectric crystal sensor which is formed and arranged to resonate at a variable frequency which is dependent on a mass loading on a crystal surface thereof;

b) introducing a test fluid into contact with the crystal surface of the sensor in the chamber;

c) controlling the temperature and/or pressure of the test fluid so as to achieve clathrate hydrate formation on the crystal surface of the sensor;

d) monitoring, directly or indirectly, change in the resonant frequency of the piezoelectric crystal sensor while said temperature and/or pressure are controlled, so as to detect a substantial change in said resonant frequency which occurs upon formation of said clathrate hydrate in the rest fluid, thereby to detect the formation of said clathrate hydrate;

e) varying one of the temperature and pressure in the chamber so as to cause dissociation of the clathrate hydrate in the rest fluid;

f) monitoring, directly or indirectly, change in the resonant frequency of the piezoelectric crystal sensor while said one of the temperature and pressure is varied, so as to detect a substantial change in said resonant frequency which occurs upon dissociation of the clathrate hydrate in the test fluid, thereby to detect the dissociation of said clathrate hydrate; and g) measuring the magnitude of the varying one of the temperature and pressure when the dissociation of said clathrate hydrate is detected, and the magnitude of the other one of the temperature and pressure, the measured magnitudes representing one of: the dissociation temperature of said clathrate hydrate in the test fluid at a particular pressure, and the dissociation pressure of said clathrate hydrate in the rest fluid at a particular temperature.

27. Method according to claim 26 wherein the method includes the following steps before or after step a):

a1) depositing a small amount of water on said sensor deposition surface;

a2) lowering the temperature in the chamber below freezing so as to freeze said small amount of water; and a3) evacuating the chamber and subsequently introducing therein a test fluid.

28. Method according to claim 26 wherein water in the form of drops, mist, or liquid is introduced into the chamber after the sensor has been placed therein.

29. Method according to claim 26, wherein the crystal surface is coated with a hygroscopic material for absorbing moisture introduced into the chamber.

30. Method according to claim 26 in which the detection of said substantial change in resonant frequency and/or rare of change of resonant frequency is achieved by recording monitored values of said resonant frequency.

31. Method according to claim 30 in which the detection of said substantial change in resonant frequency and/or rate of change of resonant frequency is achieved by recording monitored values of an electrical parameter dependent upon said resonant frequency, said parameter being selected from the group comprising current, voltage or conductance.

32. Method according to claim 26 further comprising the step of measuring the magnitude of the varying one of the temperature and pressure when said significant change in resonant frequency and/or rate of change in resonant frequency occurs, and the magnitude of the other one of the temperature and pressure.

33. Method according to claim 32, wherein the dissociation temperature (DT) at a given pressure is calculated.

34. Method according to claim 32, wherein the dissociation pressure (DP) at a given temperature is calculated.

* * * * *